United States Patent [19]

Huizinga

[11] 4,279,787

[45] Jul. 21, 1981

[54] METHOD OF BINDING ANTIGENS TO INSOLUBLE POLYMERIC SUBSTANCES

[75] Inventor: Menno Huizinga, Amsterdam, Netherlands

[73] Assignee: Tetra Consultants Inc., New Rochelle, N.Y.

[21] Appl. No.: 62,035

[22] Filed: Jul. 30, 1979

[51] Int. Cl.³ .......................... C08L 89/00; C08L 5/00
[52] U.S. Cl. ............................................ 260/8; 260/6; 260/7.5; 260/9; 260/17.4 ST; 424/12
[58] Field of Search ......................................... 260/6, 8

[56] References Cited

U.S. PATENT DOCUMENTS

| | | | |
|---|---|---|---|
| 4,045,384 | 8/1977 | Dorman | 260/8 |
| 4,119,589 | 10/1978 | Horn et al. | 260/6 |
| 4,181,636 | 1/1980 | Fischer | 260/8 |
| 4,182,695 | 1/1980 | Horn et al. | 260/6 |

*Primary Examiner*—Edward M. Woodberry

[57] ABSTRACT

This invention relates to a method of binding antigenically active materials to the surface of water insoluble, hydrophobic polymeric substances which comprises pretreating the water-insoluble hydrophobic polymeric substance with an aldehyde of the formula, OHC—X—CHO, wherein X may be $-(CH_2)_n-$, wherein n is an integer of from 1 to 10; cycloalkyl, for example, cyclopentyl, cyclohexyl; monocyclic aryl, for example, phenyl, and thereafter contacting the thus treated polymeric material with the purified antigenically active material to be bound thereto. The final products of this invention are employable as diagnostic products.

11 Claims, No Drawings

METHOD OF BINDING ANTIGENS TO INSOLUBLE POLYMERIC SUBSTANCES

This invention relates to a method of binding antigenically active material to the surface of a water insoluble, hydrophobic polymeric substance and to the novel products produced thereby.

The novel final products of this invention are particularly useful in diagnostic procedures for determining antigenic activity depending upon the antigenically active material which is bound to the polymeric substance. For example, the final products of this invention may be employed for the same purposes and in approximately the same manner as is disclosed for the products described in U.S. Pat. No. 3,995,018 and U.S. Pat. No. 3,555,143. From the disclosures and teachings set forth hereinafter, the skilled worker can easily determine how to prepare and employ the final products of this invention.

The art of binding antigenically active materials to the surface of polymeric substances is one that is well recognized in the art. Usually, this is accomplished by fixing the desired antigenically active materials to the surface of the desired polymeric substance by means of covalent bonds, under such conditions so as not to decrease or seriously alter the reactivity of the antigenically active materials being affixed.

It has now been found that by the practice of the instant invention it is possible to easily and efficiently bond to certain polymeric substances, certain antigenically active materials which previously were difficult or impossible to affix to a polymeric substrate without substantial loss of the antigenic reactivity properties for which they were to be employed. More particularly, a method has now been found which will easily and efficiently allow certain desired antigenically active materials to be bound to the surface of water insoluble, hydrophobic polymeric substances, not only without a loss in the antigenic reactivity properties of the resultant product, but with the actual enhancement thereof. I have now discovered that certain antigenically active materials may be bound to the surface of waterinsoluble, hydrophobic polymeric substances by first treating said polymeric substances with an aldehyde of the formula OHC—X—CHO wherein X may be $-(CH_2)_n$ wherein n is an integer of from 2 to 10; a monocyclic alkyl, such as cyclopentyl or cyclohexyl; a monocyclic aryl, such as phenyl, or a bicyclic aryl, such as naphthyl. The thus treated polymeric substance is thereafter reacted with the desired antigenically active material, under suitable reaction conditions, to yield the desired polymeric substance to which is affixed the desired antigenically active substance to which is affixed the desired antigenically active materials.

In the practice of the instant invention, it is required that the polymeric substance to be employed be a water-insoluble, hydrophobic polymeric substance which may be in the form of discrete particles, or sheets, films, or other forms, for example, tubes or containers. The polymeric substances which may be employed in the practice of this invention include such water-insoluble, hydrophobic polymeric substances as, polypropylene, polystyrene, polycarbonate, polyester, polyethylene, polyamide, polyacrylic acids, and other such like materials. Satisfactory results are most preferably obtained in the practice of this invention when the polymeric substance employed is either polypropylene or polystyrene, although other water insoluble hydrophobic polymeric materials also give acceptable results.

The antigenically active materials which may be employed in the practice of this invention are materials which are required to be previously purified in accordance with the process of this invention. More specifically, the practice of this invention contemplates the employment of purified antigenically active materials, which are usually comprised of proteins, lipoproteins, glycolipids, lipopolysacchrides, glycoprotein, peptides, polypeptides or carbohydrates and may be characterized as allergens. Allergens are those antigenically active materials which are associated with allergy conditions and are found in such substances as danders of animal or human origin, plant pollens, microorganisms, dusts of different varieties, tree pollens, various food products, and other like substances. Some of the allergens contemplated in this invention are disclosed in Lowenstein, Qualitative Immunoelectrophoretic Methods as a Tool for the Analysis and Isolation of Allergens, Progress in Allergy, 25th Edition (1977).

In the practice of this invention I have found that most satisfactory results are obtained when the antigenically active material employed is a purified allergen material, although other antigenically active materials also provide satisfactory results.

The final products of this invention may be prepared in accordance with the process of this invention. A water-insoluble, hydrophobic polymeric substance, for example, polypropylene, is first treated with an aldehyde of the formula OHC—(X)—CHO, wherein X may be $-(CH_2)-_n$ wherein n is an integer from 2 to 10; monocyclic alkyl, for example, cyclopentyl or cyclohexyl; monocyclic aryl, for example, phenyl; bicyclic aryl, for example, naphthyl; substituted monocyclic alkanes; or substituted monocyclic aryl, for example, tolyl. In the practice of the invention, I have discovered that the most satisfactory results are obtained when an aldehyde of the formula OHC—(CH$_2$)$_r$—CHO is employed, wherein r is an integer of from 2 to 5, and most preferably 3 or 4.

The thus aldehyde-treated polymeric substance is then reacted with the said purified antigenically active material under such mild conditions as to result in the bonding of the antigenically active material to the surface of the polymeric substance. This reaction can be obtained, for example, by incubation under low temperatures in a dilute aqueous alkaline solution, or such other methods as are known to the skilled worker to accomplish this purpose. In order to obtain the purified antigenically active material to be employed herein, a crude extract is first obtained. For example, if the antigenically active material sought to be employed herein is an allergenic material, for example, plant pollen, tree pollen, or house dust, a crude extract thereof is first obtained, by extraction, filtration or any other method suitable and known for this purpose. The crude extract may then be purified by extensive dialysis in water through membranes having porewidths of not in excess of 5,000 daltons. This dialyzed extract is then lyophilized to yield the purified antigenically active material to be employed in the practice of the instant invention.

While dialysis purification is a preferred method of purifying the crude allergenic material in the practice of this invention, there are other methods which will also provide the required purified allergenic material. Thus, any method which will successfully purify these substances by methods of separation by molecular size may be employed in the practice of this invention. Among the purification methods which may be employed in the practice of this invention are included immunoelectrophoresis, chromatographic separation, isoelectricfocusing and ion exchange chromatography, all of which are well known to the skilled worker.

The following examples are illustrative of the instant invention.

EXAMPLE 1

Pollen of the grass, *Lolium perenne*, was collected. 100grams of the thus collected pollen was then subjected to continuous extraction over a 24 hour period with 1000 ml. of a solution maintained at 4° C., of the following composition:

NaCl: 8.00 gm.
KCl: 0.20 gm.
$Na_2HPO_4$: 1.15 gm.
$KH_2PO_4$: 0.20 gm.
Phenol: 5.00 gm.
Pyrogen-free distilled $H_2O$: q.s. 1000 ml.

The resultant extract solution was then filtered through Whatman No. 1 filterpaper and then successively through membranes filters having the following pore widths: 8 um, 5 um, 1.2 um, 1.0 um, 0.8 um, 0.6 um, 0.4 um, 0.3 um, and 0.2 um.

The thus extracted and filtered pollen extract was then purified by the dialysis thereof for 7 hours against 20 liters of distilled water maintained at 4° C., through a membrane having a pore width of 5000 daltons. (Commercially available from Amicon Co. under tradename HIP.5.)

The thus dialyzed extract solution was then taken to dryness by lyophilization. The dried purified pollen extract weighted two grams.

EXAMPLE 2

The procedure of Example 1 was followed except that for the grass pollen employed therein, there was substituted the following antigenically active material which yielded the purified dried material set forth in Table 1 below:

TABLE 1

| Antigenically Active Materl (100 gm.) | Yield of Purified Material (gm.) |
|---|---|
| Oaktree pollen | 1.4 |
| Dandelion pollen | 6.0 |
| Spruce fir tree pollen | 1.6 |
| Mugroot pollen | 5.2 |
| Birch tree pollen | 1.7 |
| Goosefoot pollen | 2.8 |
| Cock's foot pollen | 2.5 |
| Dog hair allergen | 0.1 |
| Guinea pig hair allergen | 0.05 |
| Human hair allergen | 0.1 |
| Horse hair allergen | 0.1 |
| Cat Hair allergen | 0.05 |
| Rabbit Hair allergen | 0.03 |
| House dust allergen | 0.006 |

EXAMPLE 3

A solution of the following composition was prepared:

Glutaraldehyde: 2 mg/l.
$Na_2CO_3/NaHCO_3$: 0.1 M
Distilled $H_2O$: q.s. 100 ml.
pH: 9.0

One ml. of the thus prepared solution is then added to each of 100 polypropylene tubes (50×100 mm) and reacted therewith over a 4 hour period at 56° C., by gently shaking in a waterbath. The thus treated tubes were allowed to cool to room temperature whereupon the contained solution was removed by suction.

EXAMPLE 4

The procedure of Example 3 was followed except that equivalent amounts of the following polymeric substances were substituted for the polypropylene tubes, yielding equivalent results, polystyrene, polycarbonate, polyethylene, polyamide.

EXAMPLE 5

The procedure of Example 3 was followed except that equivalent amounts of the following aldehydes were substituted for glutaraldehyde yielding like results: adipaldehyde, phthalaldehyde, toluenedicarbaldehyde, benzenediacetaldehyde, cyclohexanedicarbaldehyde, naphthalenedicarbaldehyde.

EXAMPLE 6

A solution of the following composition was prepared:

Dried purified pollen extract of Example 1: 10 mg/l.
$Na_2CO_3/NaHCO_3$: 0.1 M
Pyrogen-free distilled water: q.s. 100 ml.
pH: 9.0

One ml. of the resultant solution is added to each of the polypropylene tubes obtained in Example 3 and the tubes are incubated therewith over a 24 hour period at 4° C. Thereafter, the solution is removed from the tubes by suction, and they are each washed three times with one ml. of a solution having the following composition; and the washed tubes are thereafter allowed to dry.

NaCl: 8.0 gm.
KCl: 0.2 gm.
$Na_2HPO_4$: 1.15 gm.
$KH_2PO_4$: 0.2 gm.
Distilled $H_2O$: q.s. 1000 ml.

EXAMPLE 7

100 grams of polystyrene beads having an average diameter of 2–20 um were treated with 10 ml. of a solution of the following composition:

Glutaraldehyde: 5 mg/l.
$Na_2CO_3/NaHCO_3$: 0.1 M
Distilled $H_2O$: q.s. 100 ml.
pH: 9

The beads were treated with the said solution over a period of four hours at a temperature of 56° C. After cooling to room temperature, the solution is removed and the beads were washed three times with 10 ml. of the washing solution prepared in accordance with the procedures set forth in Examply 6. The washed polystyrene beads were then treated over a 24 hour period at 4° C., with a solution of the following composition:

Dried purified oaktree extract of Example 2: 100 mg/l.
$Na_2CO_3/NaHCO_3$: 0.1 M
Distilled $H_2O$: q.s. 1000 ml.
pH: 9.0

The thus treated polystrene beads were then washed three times with the washing solution of Example 6, and allowed to dry.

EXAMPLE 8

The polypropylene tubes obtained in Example 6 are each then incubated for 6 hours at 4° C., with one ml. of a solution of the following composition:
Human serum albumin: 40 mg/l.
NaCl: 8.0 gm/l.
KCl: 0.2 gm/l.
$Na_2HPO_4$: 1.15 gm/l.
$KH_2PO_4$: 0.2 gm/l.

The incubated tubes are then washed three times with the washing solution prepared in accordance with Example 6 and the tubes dired. This procedure is performed to insure consistent results and to prevent absorption of undesirable proteins upon use of the final product.

EXAMPLE 9

The procedure of Example 8 is followed except that 10 grams of the polystyrene beads obtained in Example 7 are substituted for the polypropylene tubes, and the polystyrene beads are incubated with 10 ml. of the albumin solution of Example 8.

EXAMPLE 10

In order to test for antigenic activity, the polymer to which the antigenic material is bound is incubated over a period of 4 hours with a quantity of serum of a patient sensitized for the test antigen. After incubation, the serum is removed and the polymeric material washed with a washing solution such as set forth in Example 6. The washed polymer was then incubated with an amount of anti-IgE-$I^{125}$ of known count for 24 hours, after which the incubated polymer was washed and dried. The resultant polymer was then tested for radioactivity in a gamma counter; the standard activity being rated at 100 and no activity being rated at 0.

The polypropylene tubes obtained in Example 8 and the polystyrene beads obtained in Example 9 were tested for allergenic activity according to the above procedure. In addition, the activities of these final products were compared to other products not prepared in accordance with this invention with the following results:

| Product | Activity |
| --- | --- |
| Polypropylene tubes of Example 8 | 100 |
| Polypropylene tubes with crude unpurified pollen extract | 0 |
| Polypropylene tubes with purified pollen extract but without aldehyde pretreatment | 60 |
| Polystyrene beads of Example 9 | 100 |
| Polystyrene beads with crude unpurified pollen extract | 0 |
| Polystyrene beads with purified pollen extract but without aldehyde pretreatment | 70 |

The foregoing demonstrates the unique and improved results obtained with the instant invention.

The instant invention may be variously otherwise encompassed within the scope of the following claims.

What is claimed is:

1. A method for affixing antigenically active material to the surface of a water insoluble hydrophobic polymeric substance which comprises first treating the surface of the water insoluble hydrophobic substance with an aldehyde of the formula OCH—(X)—CHO, where —(X)— may be alkylene, cycloalkyl, aryl, substituted cycloalkyl or substituted aryl; and then reacting the thus treated polymeric substance with a purified antigenically active material in order to bond said biologically active material to the surface of said polymeric substance.

2. The method of claim 1 wherein the aldehyde is of the formula OHC—$(CH_2)_n$—CHO, wherein n is an integer of from 2 to 10.

3. The method of claim 1, wherein n is an integer of from 3 to 5.

4. The method of claim 1 wherein the polymeric substance may be polypropylene, polystyrene, polycarbonate, polyethylene, polyester, polyacrylic acids, or polyamides.

5. The method of claim 1 wherein the purified antigenically active material is an allergen.

6. The method of claim 1 wherein the antigenically active material is purified by dialysis and is comprised of protein, glycoprotein, polyprotein, peptide or carbohydrate materials derived from living organisms.

7. The method of claim 1 wherein the antigenically active material is purified by dialysis against water and then lyophilized.

8. A water insoluble, hydrophobic polymeric substance which has affixed to the surface thereof a purified antigenically active material, produced in accordance with claim 1.

9. The method of claim 1 wherein the polymeric substance is polypropylene or polystyrene.

10. The method of claim 1 wherein the aldehyde is selected from the group consisting of glutaraldehyde, adipaldehyde, phthaladehyde, toluenedicarboaldehyde, benzenediacetaldehyde, cyclohexanedicarbaldehyde and naphthalenedicarbaldehyde.

11. The method of claim 1, wherein the aldehyde is glutaraldehyde.

* * * * *